(12) United States Patent
Thierman (10) Patent No.: US 8,364,246 B2
(45) Date of Patent: Jan. 29, 2013

(54) COMPACT FEATURE LOCATION AND DISPLAY SYSTEM

(75) Inventor: Jonathan S. Thierman, Baltimore, MD (US)

(73) Assignee: Sure-Shot Medical Device, Inc.

( * ) Notice: Subject to any disclaimer, the term of this patent is extended or adjusted under 35 U.S.C. 154(b) by 995 days.

(21) Appl. No.: 11/854,866

(22) Filed: Sep. 13, 2007

(65) Prior Publication Data

US 2009/0076380 A1    Mar. 19, 2009

(51) Int. Cl.
*A61B 6/00* (2006.01)
(52) U.S. Cl. .......................................... 600/476; 356/4.1
(58) Field of Classification Search .................. 600/476, 600/478, 473; 356/4.01, 4.1
See application file for complete search history.

(56) References Cited

U.S. PATENT DOCUMENTS

| 5,418,546 A * | 5/1995 | Nakagakiuchi et al. ........ 345/85 |
| 7,904,138 B2 | 3/2011 | Goldman et al. |
| 2006/0122515 A1 * | 6/2006 | Zeman et al. .................. 600/473 |
| 2006/0184040 A1 * | 8/2006 | Keller et al. ................... 600/476 |
| 2007/0161907 A1 | 7/2007 | Goldman et al. |
| 2007/0161908 A1 | 7/2007 | Goldman et al. |
| 2007/0162094 A1 | 7/2007 | Goldman et al. |
| 2008/0004525 A1 | 1/2008 | Goldman et al. |
| 2008/0021329 A1 | 1/2008 | Wood et al. |
| 2008/0027317 A1 | 1/2008 | Wood et al. |
| 2008/0045818 A1 | 2/2008 | Wood et al. |
| 2008/0045841 A1 | 2/2008 | Wood et al. |
| 2008/0177184 A1 | 7/2008 | Goldman et al. |
| 2008/0287806 A1 * | 11/2008 | Wood et al. .................... 600/473 |

* cited by examiner

*Primary Examiner* — Brian Casler
*Assistant Examiner* — Amanda Lauritzen
(74) *Attorney, Agent, or Firm* — Intrinsic Law Corp; Ibrahim M. Hallaj (57) ABSTRACT

The present disclosure provides systems and methods for imaging and display of features of a region of interest such as a portion of a body of a patient. A first imaging portion of the system is used to cause an interaction of an imaging beam with an underlying feature of a region of interest. A reflected or returned portion of said imaging beam is detected by a detector which then provides an output to control a display portion of the system for displaying an image corresponding to that which was detected. The system can be used for guiding or assisting clinical or industrial operations or for diagnosis of medical conditions and other uses within medicine, industry and others.

17 Claims, 6 Drawing Sheets

COMPACT FEATURE LOCATION AND DISPLAY SYSTEM

I. TECHNICAL FIELD

The present disclosure relates to imaging and visualization of features below the surface of an opaque object, for example blood vessels in tissue, and specifically in some instances to non-invasive location of the vessels in patients and projection of images of the vessels, which can be used as a clinical aid or tool.

II. BACKGROUND

The human body is supplied by a complex network of blood vessels as part of the vascular system. The blood vessels are fluid conduits allowing for flow and distribution of blood throughout the body, and are generally arranged into arterial and venous? sub-systems, which are themselves hierarchically arranged from larger ma supply vessels down to small capillary pathways. A primary function of the blood flowing through the vessels is to carry and distribute oxygen and other nutrients to the organs and tissue of the body. Another function of the blood is to collect waste products from the organs and tissue. Mechanically, the general organization of the vascular system is that of a hydraulic supply and return network with the heart providing the pumping and control to drive oxygenated blood to the organs and tissue in arteries, and to return blood from the organs and tissue in veins. Capillaries form the lowest functions on the hierarchy of vasculature, including the actual chemical (oxygen) exchange, and connect the arterial portion of the vascular network with the venous part of the vascular network.

As it carries oxygen, nutrients and waste products within the entire body, the vascular system has been recognized as a good vehicle for introducing drugs into the body, and as a good vehicle for extracting meaningful (blood) samples representative of the condition of the body. Since many primary vessels run slightly below the surface of the skin, they are accessible for procedures to introduce a substance into the blood or to extract a sample of blood from the vessels. For example, a common procedure is to introduce a drug or a fluid into the blood stream intravenously using an intravenous ("IV") line. Glucose and antibiotics are examples of things commonly injected into a patient's veins using an IV line. In practice, a medical professional inserts a needle through the skin and through one wall of a relatively large and accessible vein and the injected fluid is released into the vein through the IV needle under pressure. The converse (blood sampling) is used by pulling blood from a vein, or allowing the blood to flow out of the vein and into the needle, to draw a blood sample from a patient these procedures can be painful to people, as they involve sticking the patient with a needle. Also, inaccurate placement of a needle can lead to improper delivery of the drug or fluid, and can cause unwanted injury to vessels and tissue in the vicinity of vessels. It is therefore preferable that the needle be inserted accurately and hit its mark without undue retries. The present discussion of veins can where applicable be extended to other types of fluid vessels, for example, arteries, capillary vessels, etc.

One type of clinical procedure using the location of the appropriate vessels is the insertion of a central line, also called a central venous catheter ("CVC"). A central line is a catheter, or tube, which is inserted into a vein and physically passed through the vein to the thoracic (chest) portion of the vena cava or the right atrium of the heart. The vena cava is a large vein delivering blood to the heart. Again, proper administration of a CVC benefits from knowledge of the location of the vessels of interest.

It is therefore useful to develop methods and systems for accurate location and imaging and detection of vessels, especially to assist in medical diagnoses and procedures that employ the blood vessels such as in the applications mentioned above. It would be especially useful to overcome present limitations and provide systems that combine accuracy, clinical relevance, comfort, and at the same time are relatively inexpensive, reliable, and not excessively cumbersome. This disclosure addresses some or all of these issues.

III. SUMMARY

The present disclosure relates to visualization of things and features within objects. For example visualizing fluid conduits within solid objects or visualizing blood vessels (veins and/or arteries) within human bodies. In some respects the disclosure relates to the operation of the vascular system, e.g. in humans, but also in other animals, specifically addressing aspects of the imaging, detection and treatment of a patient condition by way of the vascular system. Existing systems that attempt to do so are excessively cumbersome, costly, ineffective, and not portable enough to be effective for all applications.

The present disclosure provides systems and methods for imaging and display of features of a region of interest, for example but not limited to, a portion of a body of a patient. A first imaging portion of the system is used to cause an interaction of an imaging beam with an underlying feature of a region of interest. A reflected or returned portion of said imaging beam is detected by a detector which then provides an output to control a display portion of the system for displaying an image corresponding to that which was detected. The system can be used for guiding or assisting clinical operations or for diagnosis of medical conditions and other uses within medicine, industry and others One particular embodiment is directed to an imaging system for imaging a region of interest, including an imaging light source providing an imaging light beam including light in a first range of the electromagnetic spectrum, an incident portion of said imaging light being suitable for optical interaction with an underlying feature of said region of interest and suitable to provide a return portion of said icing light following an optical interaction of said imaging light beam with said underlying feature; a detector adapted and arranged to detect a magnitude of a characteristic of said return portion of said imaging light and adapted to provide an output signal corresponding to said magnitude; a display light source providing a display light beam including light in a second range of the electromagnetic spectrum, the display light beam being suitable for projecting an image onto a surface of said region of interest; a controller adapted and arranged to receive the output signal from said detector and provide a control signal to control a characteristic of said display light beam; and a scanner for scanning said imaging and display light beams across said region of interest.

Another particular embodiment is directed to a method for detecting and generating a visual representation of a feature beneath the surface of an object, including generating an imaging light beam; controllably scanning said imaging light beam across at least a portion of said surface; detecting a characteristic of a returned portion of said imaging light beam which has interacted with said feature beneath the surface of the object; generating a control signal corresponding to a characteristic of said returned portion of said imaging light beam; generating a display light beam and modulating a characteristic of said display light beam using said control signal; and controllably scanning said display light beam across at least said portion of said surface so as to visibly represent said feature on said surface of said object.

V. DETAILED DESCRIPTION

Figure 1:
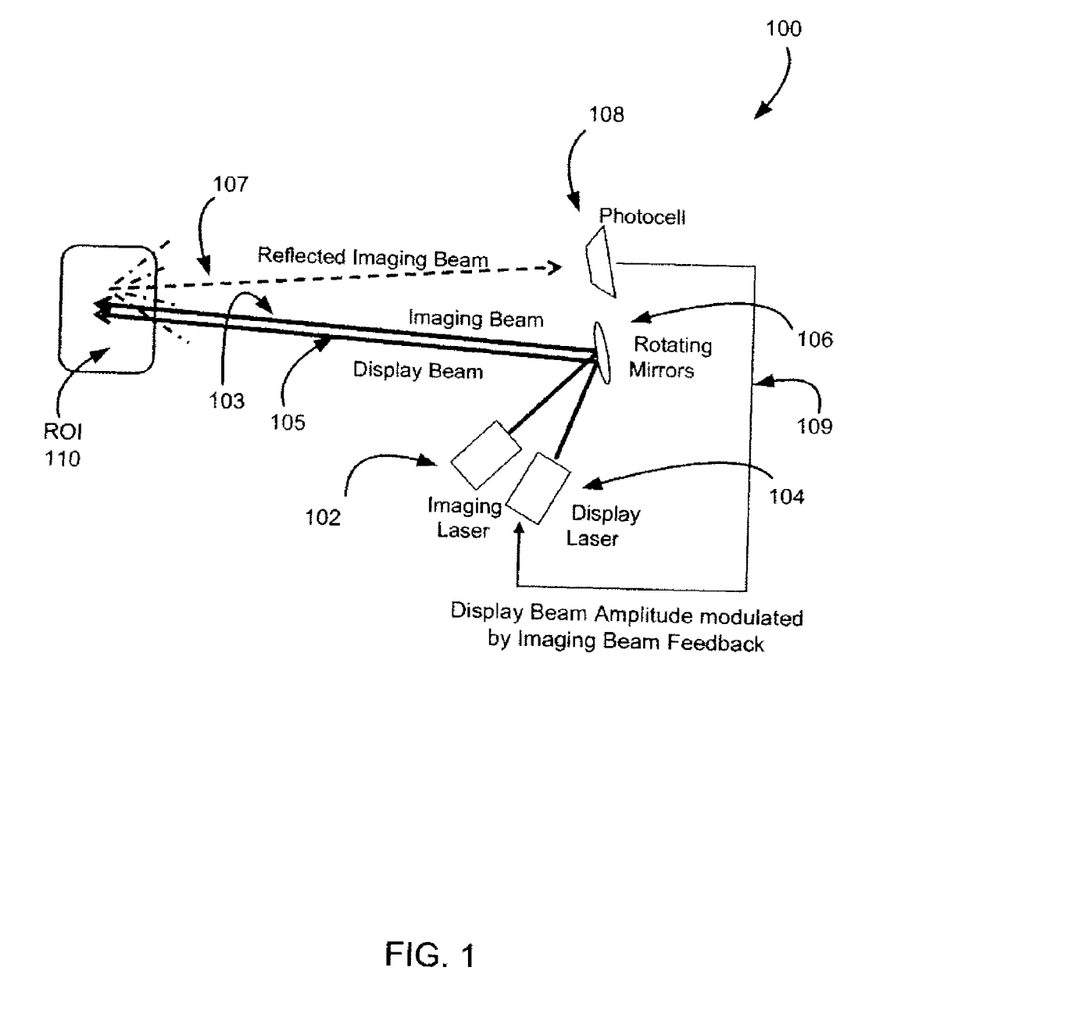
FIG. 1 illustrates an exemplary embodiment of a vascular location and projection system.

FIG. 1 illustrates an exemplary embodiment of a vascular location and projection system 100. The system includes an imaging laser 102, which provides a coherent laser light output in an appropriate frequency range for imaging the vascular system in patients. The system also includes a display laser 104, which provides a coherent laser light output in an appropriate frequency range for display of an image, typically in a visible range of the electromagnetic spectrum (i.e., having a wavelength between about 400 and 700 nm). The imaging laser 102 is generally used to obtain the location of the vessels of a patient, while the display laser 104 is generally used to indicate to a medical practitioner or user of the system 100 the location of the imaged vessels. In some embodiments, the location of the imaged vessels is substantially overlaid in a projection by display laser 104 onto the body of a patient so that the projected image of the vessels is outlined onto the surface of the patient's body (skin) and generally maps to the actual location of the vessels below the surface. In this way, a practitioner (surgeon, blood technician, emergency injection operator, etc.) can easily locate the vessels below the surface of the skin and access the vessels as necessary, with the desired accuracy, to accomplish their task.

One or more rotating mirrors 106 are used to direct the light output of the imaging and display lasers, 102 and 104 respectively, onto the desired location of the patient's body. Note that the rotating mirrors 106 can be augmented with other optical components such as other lenses, gratings, optical elements, apertures, gates, relays, mirrors, including flat, concave, convex, or combinations thereof to achieve the desired guidance of the light onto and collection of light from the patient's body. This can include focusing or defocusing elements, filters, amplifiers, and other optical components as called for in a particular design of the system 100. The overall result of the one or more optical elements is an optical assembly that provides an imaging beam 103 by which the patient is irradiated and which is incident upon a region of interest ("ROI") of the patient's body. One method of achieving the transmission of the incident beam over a rectangular ROI on the skin is by means of a pair of mirrors which rotate in orthogonal planes and which redirect the laser beam in a controlled raster-scan pattern over an x and y coordinate axis projected onto the skin. The imaging beam 103 operates on and interacts with the patient's vasculature and/or blood and provides the imaging of the vascular system in the ROT 110. In addition, the optical assembly (or a separate optical assembly if the aging and display paths are treated separately) carries a display beam 105 that is used to display the relevant image of the vascular system of the ROI 110. In some embodiments, the display beam 105 and imaging beam 103 propagate along parallel but spatially distinct optical paths. In other embodiments both the display and imaging beams 105, 103 propagate substantially along the same optical path and use shared optical components.

In operation, the imaging beam 103 is incident upon a ROT 110 on the patient's body as mentioned above. The light from the imaging beam 103 penetrates the patients skin and outer tissues so as to be incident on and interact with the patient's vascular system and/or the blood within the patient's vascular system in the ROI 110. The light from imaging beam 103 is then redirected, reflected, refracted, and otherwise sent upon its interaction with the patient's vascular system and/or blood in the ROI 110 back out from the patient's body in what we refer to herein as the "reflected imaging beam" 107. In one embodiment, near-infrared light is used which is known to have a higher absorption coefficient by blood than by other tissue. It should be appreciated that while reflection and absorption is one way of forming the reflected imaging beam 107, other optical and electromagnetic, chemical, and mechanical effects influencing the incident imaging beam 103 can also contribute to or influence the light forming the reflected imaging beam 107. The intensity of the reflected beam is a function of the absorption and scattering of the incident beam by the tissue and blood upon which it is incident at each location in the ROI as the incident beam is controllably scanned across the ROI.

The reflected imaging beam 107 is sensed by a photocell 108. More specifically, light forming the reflected imaging beam 107 is collected by some optical assembly that can include a lens, collator, filter, modulator, mirror, prism shaped collector, and other optical elements for delivery to a photocell 108, directly or indirectly. The photocell 108 can be of a number of sizes and configurations so that it can sense an intensity, power, amplitude, or other quantifiable characteristic of the reflected imaging beam 107. Photocell 108 may include an array or grid of photo-sensitive elements, e.g. arranged in two dimensions such as x-y Cartesian dimensions to form an output signal 109. When measured by a photodetector as a function of time (which can be directly related to the position of the incident beam in the ROI as it is scanned across the region), the signal intensity from the reflected beam can be used to recreate a map of the tissue reflection and absorption as a function of location in the ROI. Note that in some embodiments, the use of a line-source or spot/pencil beam source of light can be accomplished where the line or pencil beam sources are scanned with a mechanical or opto-electro-mechanical scanner so as to cover the surface of the ROI by translating the location of the spot or line beam over the surface of the ROI.

In turn, the photocell output 109 includes one or more signals that can be used to modulate the display laser 104 and hence modulate display beam 105. It can now be seen that the display portion of the system 100 is modulated by the imaging portion of the system 100 such that the images projected by the display portion of the system 100 can include information derived from the imaging portion of the system 100. In particular, in some embodiments, the display portion of the system 100 can be made to project an image of or light information representative of the blood vessels in the ROI 110. Even more particularly, a visible light image can be projected onto the surface of the patient's body that is effectively a representation that is spatially and visually matched to or corresponding to the blood vasculature beneath the ski in the ROI 110, where a light-coded portion of the projected image corresponds to an underlying vessel located directly beneath the light-coded portion of the projected image.

In one embodiment, the intensity of the projected display light beam 105 is modulated to spatially indicate on the patient's body in the ROI 110 the location of an underlying vein (or vessel that is to be injected or otherwise used in a medical procedure such as insertion of an IV line. In another embodiment, the inverse image (the negative) is possible, where the path and location of a blood vessel is darkened relative to the surrounding portion of the ROI 110. In yet another embodiment, a color-coding is used in a multi-color modulated display system to indicate various features of the vascular system being imaged. For example, characteristics of the vascular system including temperature, flow rate, oxygen level diameter, pressure, proximity to the surface, and other characteristics of the vessels and vascular network can be indicated by proper modulation of the imaging portion of the system 100.

As to the design of the rotating mirror assembly 106, this allows single line or planar scanning of a region of interest over a finite surface of the patients body so that a single and relatively simple laser can be used for the imaging laser 102. In the same way, a relatively simple source can be used for the display laser 104 so that it can be used to cover and illuminate and form a projection onto a finite area of the ROI 110 of the patient's body. The operation of the rotating mirror can be controlled so that its speed of rotation allows a pulsed or continuous application of the laser sources 102, 104, to achieve a controlled result on the patient's body in the ROI 110. In one embodiment, the image and display lasers use the same rotating mirror assembly to minimize the number of parts and to ensure perfect collocation of the two laser beams on the ROI.

The display laser 102 itself can also be made of one or more parts so as to project an image (e.g., a two-dimensional image) or representation upon the patient's body's ROI 110. The display portion of the system 100 can be specifically built to include a microdisplay, digital projection elements, microreflectors, etc. that are controllable and addressable to form two-dimensional light output in display beam 105 that is indicative of the vascular structure being imaged. The modulation of the display portion of the system 100 can be amplitude modulation with a resulting dark-to-bright modulation of specific areas of the illuminated image corresponding to characteristics of the vascular system in the patient's body in the ROI 110.

Figure 2:
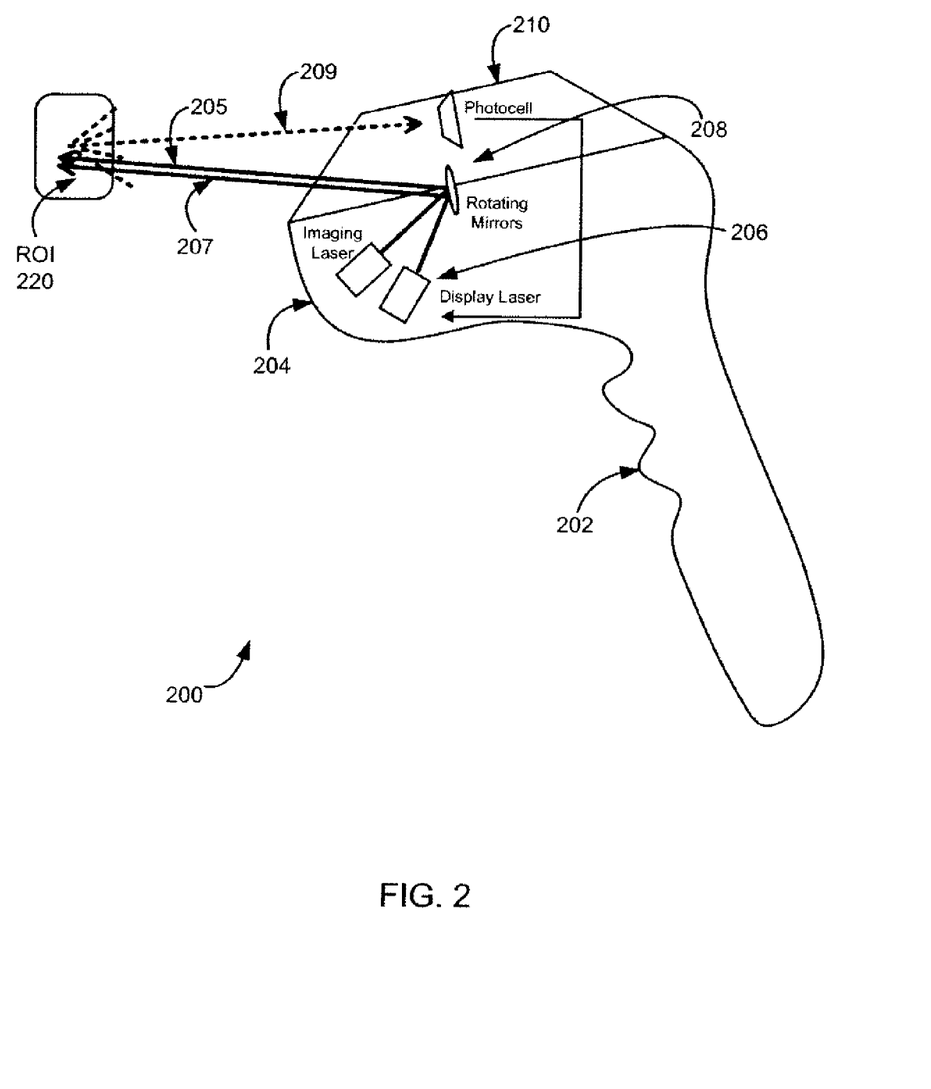
FIG. 2 illustrates an exemplary compact and portable blood vessel location and image projection system.

FIG. 2 illustrates an exemplary compact and portable blood vessel location and image projection system 200 that is meant to be low-power and hand-held. This application can be used in the field for military (e.g., combat) or civilian (e.g., emergency services) operations to locate blood vessels below the surface of a patient's skin under various conditions. A hand grip and housing 202 can be of several forms such as a gun-style form that can be further clipped onto a belt stowed in a holster, or otherwise kept ready for use.

The system 200 can be portable, light-weight and powered by a DC power source such as a battery. The system 200 includes an imaging laser 204, emitting an imaging beam 205 in a visible or invisible wavelength range, and a display laser 206, typically emitting a visible light display beam 207 output as discussed above. The incident imaging beam 205 interacts with the vascular and/or blood of a patient's body in ROT 220 to produce a reflected imaging beam 209 that is collected and sensed by a photo-sensing assembly such as photocell 210. The photo-sensing assembly such as photo cell 210 provides an output feedback or modulation signal 212 that in turn controls the display portion of system 200 and the resulting display beam 207. Rotating mirrors 208 operate as described above, and allow for coverage of a finite area of the patient's body in ROI 220.

Figure 3:
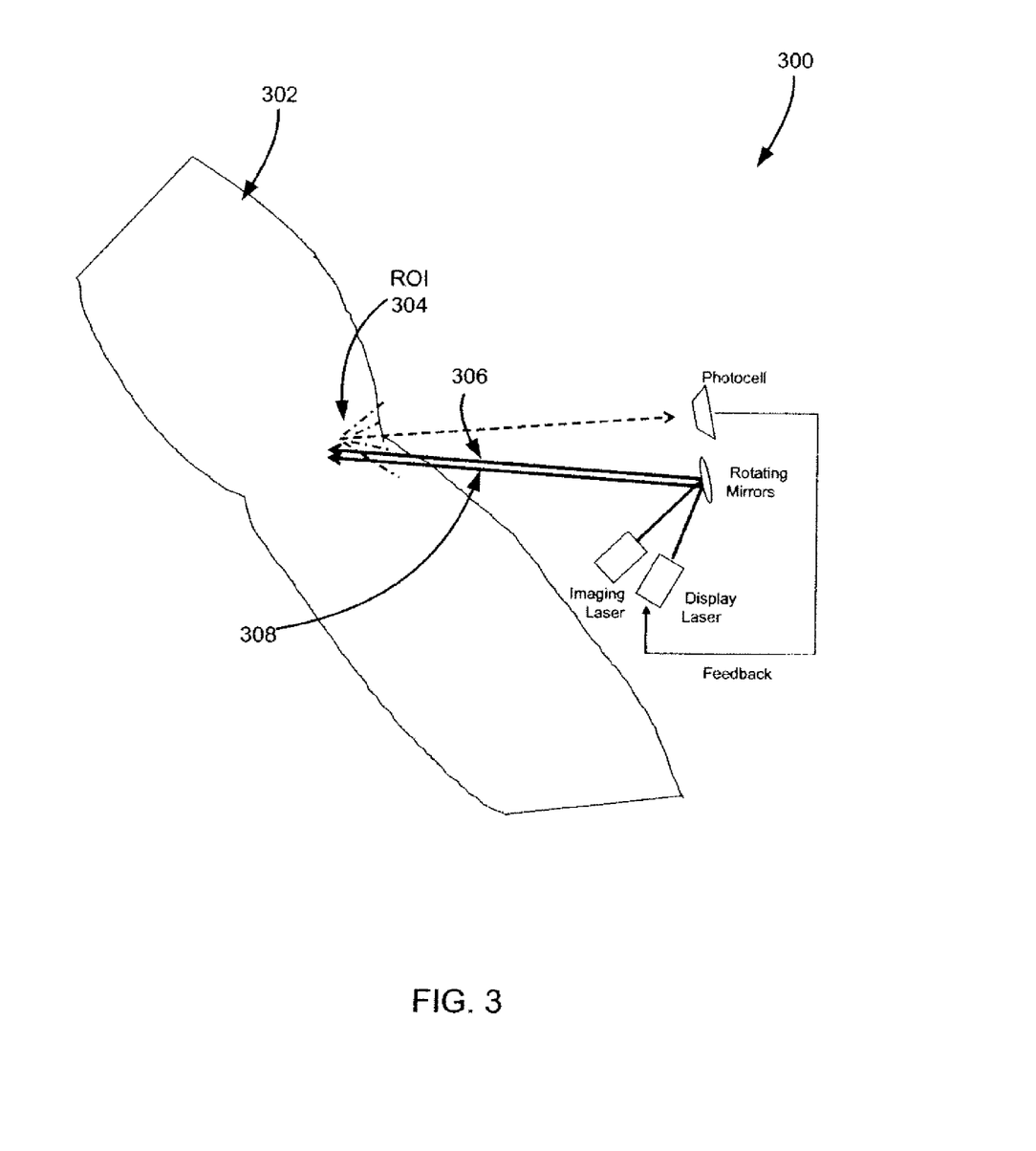
FIG. 3 illustrates an exemplary arrangement of a vascular imaging and display system in relation to a portion of a patient's body.

FIG. 3 illustrates the interaction of a vessel and/or blood imaging and display system 300 with a patients body 302, and specifically in a portion of the body identified as the region of interest or ROT 304. The ROT 304 can be a substantially two-dimensional surface of a patient's body having any of several shapes and sizes. For example, ROT 304 can extend in two Cartesian dimensions along the surface of a patient's body or skin, covering a substantially rectangular patch or aperture of said body or skin. Also, ROT 304 can extend in other coordinate systems such as a cylindrical or polar coordinate system and cover a substantially circular patch or aperture of said body or skin. Of course, in a real body, the surface covered by the ROT 304 can be generally planar (e.g., covering a small region of a human's abdomen) or can be non-planar and including topology that follows the surface of the body. Also, the ROT 304 can be considered to extend in depth into the human body underneath the skin to the extent that the imaging and/or display light beams 306 and 308 respectively penetrate below the skin.

Figure 4:
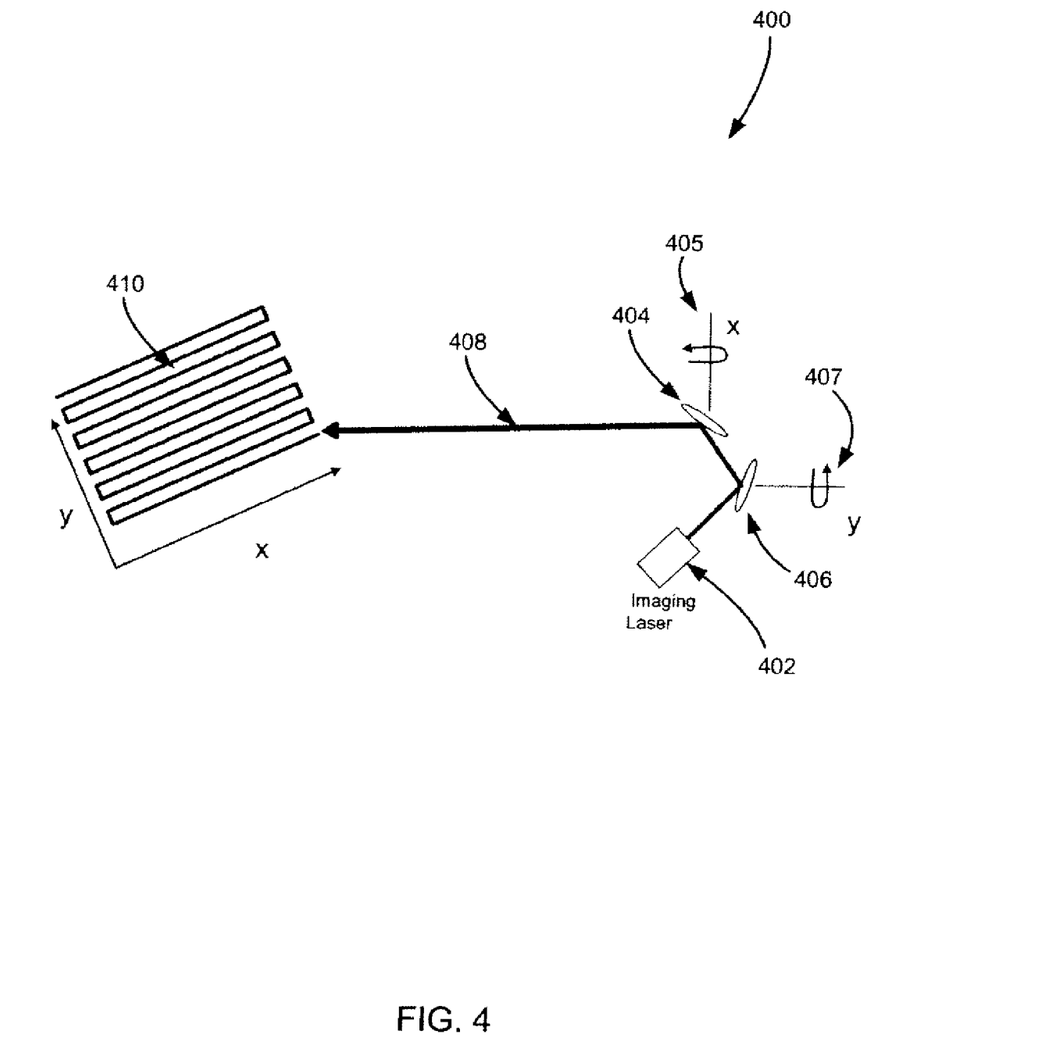
FIG. 4 illustrates an exemplary arrangement of optical components to form a raster scan of a region of interest.

FIG. 4 illustrates an exemplary embodiment of a laser imaging apparatus 400 including an imaging laser source 402. Light output from laser source 402 is directed by an optical assembly including a pair of rotating mirrors 404 and 406. First rotating mirror or mirror assembly 406 rotates about a first axis ("y") 407 and causes light scattered or reflected therefrom to pan across a line path in space perpendicular to first axis 407. The light reflected from first mirror 406 is directed towards a second mirror or mirror assembly 404 rotating about a second axis ("x") 405 and causing light reflected therefrom to pan across a line path in space perpendicular to second axis 405.

As a result of the compound or combined rotation of first and second mirrors 407 and 405, the resulting output beam 408 of the imaging laser is caused to pan or scan in a pattern 410 related to the rotations of the mirrors 407, 405. Pattern 410 generally paints a raster pattern, at any instant moving the imaging laser spot along x and y in a back and forth way so as to image the entire area covered by pattern 410.

It will be discussed below that a second light source can be similarly raster scanned across the same area as the imaging light source to project a useful visible light image onto a region of interest. In some embodiments the projected visible light can be used for locating veins (or vessels) below the surface of the skin for the purpose of medical procedures involving the veins (or vessels).

Figure 5:
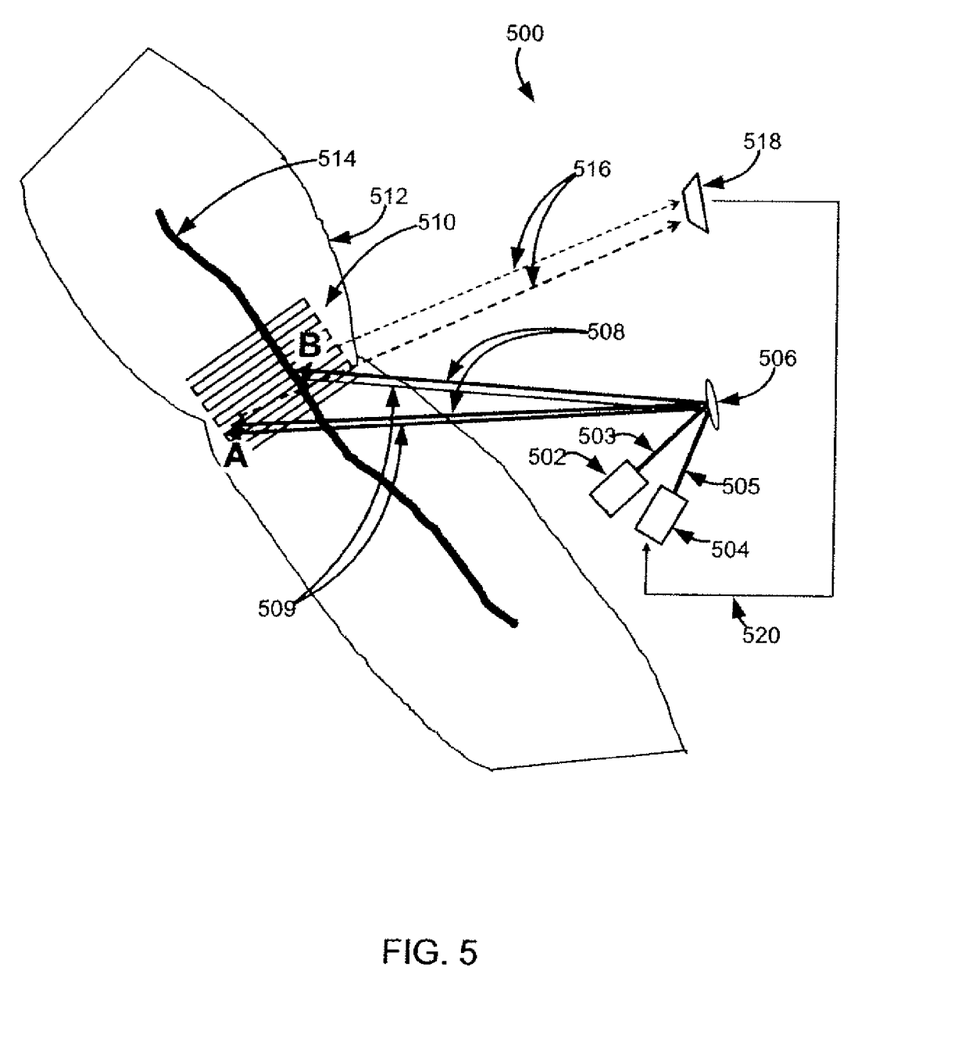
FIG. 5 illustrates raster scanning of a region of interest using an imaging and a display light source.

FIG. 5 illustrates an exemplary venous imaging and display system, or the main optical components thereof 500 as they would interact with a patient's body. An imaging laser source 502 provides a narrow or linear pencil beam of imaging light 503 in a wavelength suitable for imaging blood flowing in the patient's arm 512. An optical assembly or mirror system 506 redirects the imaging light 503 and for example includes a pair of rotating mirrors, each rotating about a separate axis such that the rotation axes for the pair of mirrors are perpendicular to one another. For example, a first mirror rotates about a horizontal axis while the second mirror rotates about a vertical axis. In this way, the pencil beam which can be generated from a simple light source without the use of complicated or expensive or voluminous diffusers can be scanned using the optical assembly as a positional scanning tool which positionally translates the location of the pencil beam over the ROT, e.g., in a raster, x-y, random or other pattern. This concept can be extended to a directed line beam that illuminates a linear portion of the ROI which is then scanned by moving across the ROI, e.g., in a x-motion, or twisting circular movement of the line beam over the ROI so as to substantially cover the ROI through a cycle of such movement of the scanner.

The scanned imaging beam 508 is taster scanned by the optical assembly 506 onto a finite area of the patient's body, painting a pattern between two points in height and two points in width for example. Imaging light penetrates the patient's skin and is incident upon an underlying vein 514 running through the patient's arm 512. As mentioned above, the present reference to veins can, where appropriate, be generalized to other vessels, e.g., arteries, etc. As the imaging beam 508 passes over the vein 514, the vein and/or the blood therein cause an optical interaction with the imaging beam 508. Therefore, the presence of the vein 514 and/or blood therein modulates an intensity and characteristics of the reflected imaging light beam 516. As depicted in the drawing, a heavy reflection of incident reflected beam 508 occurs from spot "A" where there is no vein to absorb the imaging light. However, at spot "B" where the vein is located, the imaging light beam 508 is absorbed or otherwise scattered such as the reflected imaging beam 516 is weaker or less intense when the spot is at position "B" than when the spot was at position "A."

Accordingly, photodetector 518 which detects the intensity or power of reflected imaging beam 516 can form an electrical output signal 520 which is indicative of or corresponds to or is proportional to the optical characteristics of the ROI 510 being illuminated by imaging laser 502. And hence, photodetector 518 can be used to generate an output that is the basis for forming an image of the optical characteristic (e.g., absorption coefficient, reflectivity, etc.) of the tissue in ROI 510. This modulation and systematic scanning of ROI 510 can be therefore used to generate an "image" that indicates where blood or blood vessels are located below the surface of the skin irradiated by imaging laser beam 509. Once collected, the age can be stored, transmitted, processed, or delivered to a display apparatus such as a computer display monitor.

In addition, the electrical output signal 520 from photodetector 518 can be used to modulate the power or intensity of a second light source (e.g., LED laser source) 504 referred to as a display light source. The display light source 504, being provided with the output electrical signal 520 as a feedback or modulating signal, delivers a beam of light referred to as a display light 505 onto optical assembly (e.g., rotating mirrors) 506. The rotating mirrors 506 paint or scan the reflected display beam 509 onto the ROI 510 in a way that is the same or similar to how the imaging beam 508 was scanned. The result is a raster scanned image of the underlying optical features of ROT 510 being projected onto the surface of ROI 510. In this way, if the imaging beam is in a wavelength range that is not visible but the display beam is in a wavelength that is visible, the operator of apparatus 500 can see with his or her bare eyes, and essentially in real time, an image of the venous system of the patient within ROI 510. This process is non-invasive, safe, inexpensive and can be made with relatively compact and durable components for use in clinical and field applications.

Figure 6:
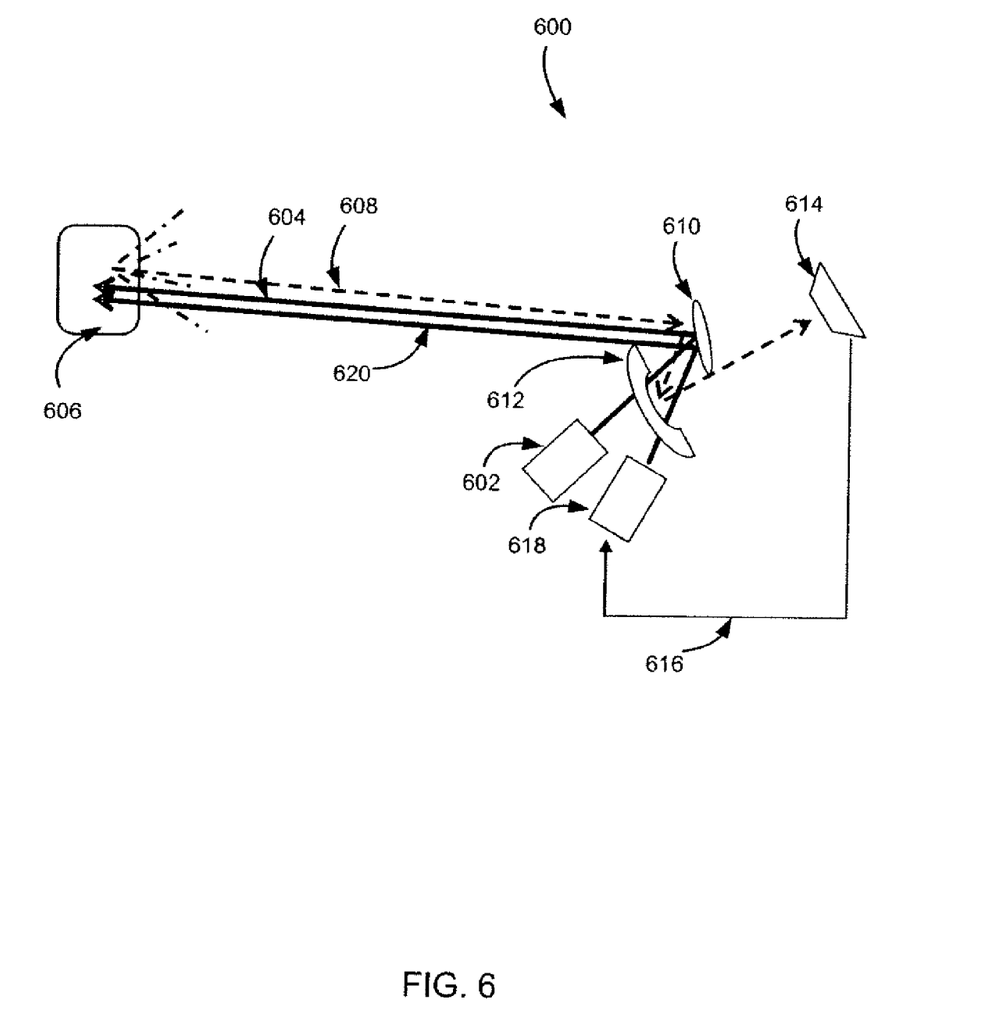
FIG. 6 illustrates an exemplary embodiment employing an optical collector or reflector for collecting light for the photo detector.

FIG. 6 illustrates an exemplary compact apparatus 600 for detecting and displaying a vessel or other feature of interest within a region of interest ROI 606, which can be a portion of a human patient's body, an animal's body, a plant, or non-living structure within which lies or runs a feature that can be imaged as described herein. An imaging laser light source 602 sends out an imaging light beam 604 which is directed by an optical assembly including a rotating prism lens or mirror 610 and prism, lens, mirror, collector or reflector 612 to reach ROT 606. As discussed herein, the incident imaging beam 604 is scattered, reflected, or otherwise affected within ROT 606 to cause a reflected beam of light 608 which carries in its characteristics (e.g., intensity, power) information relating to the underlying features of ROI 606.

An optical assembly that can include at least one prism, lens or error 610 and/or at least one prism lens, or mirror collector or reflector 612 captures some or all of reflected imaging beam 608 and delivers such light towards a photo detector 614. The photo detector 614 as discussed herein can provide an output signal 616 which is used to modulate or control display laser source 618. This modulation or control is used to affect a characteristic (e.g., intensity, power) of display light beam 620 which is sent towards ROI 606, optionally by way of the optical assembly (e.g., 610, 612).

In one aspect, the optical assembly is used three times in an imaging/detection and display process. First, the optical assembly is used to direct the imaging light beam onto the ROI. Second, the optical assembly is used to capture reflected light that is substantially co-linear with the incident imaging light beam. This can in some instances improve the collection and detection of relevant light in low signal-to-noise environments, and can be of use in environments where the ROI includes a reflector. In this situation, the reflected light beam can be considered a "retroreflected" beam but for the present purposes is collectively considered "reflected." The third use of the optical assembly in a detection-display sequence is to direct the display light beam onto the correct portion of the ROI as discussed above.

It should be appreciated that the overall operation of the present imaging and display systems can be controlled by the construction of the system and by the method for applying the system to the patient's body. For example, the overall power and intensity of the imaging beam and the optical wavelengths used in the imaging portion of the system can affect the physical characteristics to which the system and imaging light responds. For example, using other wavelengths, e.g., infrared light, or near-infrared light, to image the body can provide deeper penetration into the body depending on the application and the type of tissue intervening between the light source and the feature being detected.

It should also be appreciated that the wavelength of the imaging and the display light beams do not have to be the same. For example, the imaging light may be in the infrared while the display light may be in the visible range of the electromagnetic spectrum, allowing plain-sight observation of the displayed image projected onto the ROI. Auxiliary features and functions can be microprocessor controlled and can include the ability to control the intensity of the imaging and the display portions of the system.

The present system and methods can be applied to more than just imaging of veins, arteries, and vessels in a human or animal body. But with proper selection of inking light source power and wavelength and system design the system can image piping and vessels and flow paths and other features hidden from view. For example, for inspection of circuit boards, fluid pipes, wear on parts, or other thermal or corrosive environments best imaged with ultraviolet ("UV") or infrared ("IR") or other light sources. A light source optimized in frequency and other characteristics to image the feature or object disposed below the skin or skin and subcutaneous fat layers or other tissue can be used.

In addition, there can be safety and architectural and manufacturing applications of the present systems and features. In addition to those already discussed such as IV and central line placement, some specific applications which the present system can be adapted for include: infrared ("IR") spectroscopy for chemical identification and blood analysis, for glucose and metabolic monitoring, for treatment of bleeding patients or those having internal bleeding, intraoperative use to avoid unwanted cutting of blood vessels during surgery, dermatological use for assessing ulcer vascularization and other possible uses of IR or UV signal from the skin to assess melanoma, differentiate malignant/benign, assess skin health from sun damage, deeper thermal imaging of sinuses in suspected sinusitis to assess for blood, visualizing varicosities and other telangiectasia of the venous system. In addition, the system could be adapted for use in biometric security applications such as personal identification and secure access applications where a unique or detectable blood vessel or pattern of blood vessels or other biometric characteristic is sensed and indicated.

Numerous other embodiments, modifications and extensions to the present disclosure are intended to be covered by the scope of the present inventions as claimed below. This includes implementation details and features that would be apparent to those skilled in the art upon review of the present disclosure and appreciation of the concepts and illustrative embodiments provided herein.

What is claimed is:

1. An imaging system for imaging a region of interest, comprising:
    an imaging light source providing an imaging light beam including light in a first range of the electromagnetic spectrum, an incident portion of said imaging light beam being suitable for optical interaction with an underlying feature of said region of interest and suitable to provide a return portion of said imaging light beam following an optical interaction of said imaging light beam with said underlying feature;
    a detector configured to detect a magnitude of a characteristic of said return portion of said imaging light beam and configured to provide an output signal corresponding to said magnitude;
    a display light source providing a display light beam including light in a second range of the electromagnetic spectrum, the display light beam configured to project and image onto a surface of said region of interest;
    a controller configured to receive the output signal from said detector and provide a control signal to control a characteristic of said display light beam;
    a scanner configured to spatially scan said imaging and display light beams across said region of interest; and
    an optical assembly configured to redirect said imaging light beam and said display light beam from their respective sources onto said region of interest and to redirect said portion of said imaging light beam from said region of interest onto said detector, said optical assembly further comprising optical components including a light collector disposed and designed to collect only a selected portion of said return portion of light returned by said region of interest and being substantially returned along a direction substantially co-linear with a direction of said incident imaging beam.

2. The system of claim 1, said first range of the electromagnetic spectrum comprising a non visible range of the electromagnetic spectrum.

3. The system of claim 2, said first range of the electromagnetic spectrum including an infrared range of the electromagnetic spectrum.

4. The system of claim 2, said first range of the electromagnetic spectrum including a near-infrared range of the electromagnetic spectrum.

5. The system of claim 1, said second range of the electromagnetic spectrum including a visible range of the electromagnetic spectrum.

6. The system of claim 1, said imaging light source comprising a laser light source.

7. The system of claim 2, said display light source comprising a laser light source.

8. The system of claim 2, said display light source comprising an LED projection source.

9. The system of claim 1, adapted in a portable housing for imaging a region of interest on a patient's body within a clinical or field application for treating patients.

10. The system of claim 1, further comprising an electromechanical driver configured to cause an angular movement any of said optical assembly or scanner about at least one axis of rotation.

11. The system of claim 1, said scanner comprising at least one mirror for reflecting at least one of said imaging light beam and display light beam onto said region of interest.

12. The system of claim 1, said scanner comprising a pair of rotating mirrors for reflecting at least one of said imaging light beam and display light beam onto said region of interest in a substantially two-dimensional scanned pattern.

13. The system of claim 1, said characteristic of said underlying feature comprising an optical characteristic affecting said magnitude of said characteristic of said return portion of said imaging light.

14. The system of claim 1, said detector comprising at least one photodetector that detects an intensity or power of said return portion of said imaging light.

15. The system of claim 1, said controller modulating an output power or intensity of said display light beam.

16. The system of claim 1, said scanner comprising an assembly constructed and arranged to controllably direct and translate a pencil-beam light spot over at least a portion of the region of interest.

17. The system of claim 1, said scanner comprising an assembly constructed and arranged to controllably direct and translate a line-beam light source over at least a portion of the region of interest.

* * * * *